(12) United States Patent
Komatsu et al.

(10) Patent No.: US 8,889,830 B2
(45) Date of Patent: Nov. 18, 2014

(54) HEMOGLOBIN-ALBUMIN COMPLEX, AND ARTIFICIAL PLASMA EXPANDER AND ARTIFICIAL OXYGEN CARRIER CONTAINING THE COMPLEX

(75) Inventors: Teruyuki Komatsu, Hino (JP); Daiki Tomita, Saitama (JP)

(73) Assignee: Chuo University, Tokyo (JP)

( * ) Notice: Subject to any disclaimer, the term of this patent is extended or adjusted under 35 U.S.C. 154(b) by 0 days.

(21) Appl. No.: 14/002,471

(22) PCT Filed: Feb. 20, 2012

(86) PCT No.: PCT/JP2012/001118
§ 371 (c)(1),
(2), (4) Date: Aug. 30, 2013

(87) PCT Pub. No.: WO2012/117688
PCT Pub. Date: Sep. 7, 2012

(65) Prior Publication Data
US 2013/0338342 A1    Dec. 19, 2013

(30) Foreign Application Priority Data
Mar. 1, 2011   (JP) ................................ 2011-044207

(51) Int. Cl.
*C07K 14/00* (2006.01)
*C07K 14/765* (2006.01)
*C07K 14/805* (2006.01)
*A61K 38/00* (2006.01)

(52) U.S. Cl.
CPC ............. *C07K 14/765* (2013.01); *C07K 14/805* (2013.01); *C07K 2319/31* (2013.01); *A61K 38/00* (2013.01)
USPC .......................................... 530/363; 530/385

(58) Field of Classification Search
CPC ............... C07K 14/765; C07K 14/805; C07K 2319/31; A61K 38/00; G01N 33/543
USPC .................................................. 530/363, 385
See application file for complete search history.

(56) References Cited

U.S. PATENT DOCUMENTS

2006/0247423 A1   11/2006   Su et al.
2008/0032417 A1*   2/2008   Olejnik et al. ................ 436/173

FOREIGN PATENT DOCUMENTS

| JP | A-8-301873 | 11/1996 |
| JP | A-10-306036 | 11/1998 |
| JP | A-11-502821 | 3/1999 |
| JP | A-2004-307404 | 11/2004 |
| JP | A-2005-515225 | 5/2005 |
| JP | A-2006-516994 | 7/2006 |

OTHER PUBLICATIONS

Hu et al., "Bovine Serum Albumin-Bovine Hemoglobin Conjugate as a Candidate Blood Substitute," *Biotechnology Letters*, 2002, vol. 24, No. 4, pp. 275-278.
Hu et al., "A Solid Phase Adsorption Method for Preparation of Bovine Serum Albumin-Bovine Hemoglobin Conjugate," *Journal of Biotechnology*, 2003, vol. 100, No, 3, pp. 267-275.
Zheng et al., "The Role of pH and its Control on Effective Conjugation of Bovine Hemoglobin and Human Serum Albumin," *Process Biochemistry*, 2007, vol. 42, No. 3, pp. 303-309.
Lu, et al. "Conjugate of Bovine Hemoglobin and Human Serum Albumin as a Candidate for Blood Substitute," *Artificial Blood*, 2005, vol. 13, No. 2, p. 61.
Kai et al., "Development of Totally Synthetic Artificial Oxygen Carrier," *Artificial Blood*, 2005, vol. 13, No. 1, pp. 34-41 (with Abstract).
International Search Report issued in International Patent Application No. PCT/JP2012/001118 dated Mar. 27, 2012.

* cited by examiner

Primary Examiner — Chih-Min Kam
(74) Attorney, Agent, or Firm — Oliff PLC

(57) ABSTRACT

A novel hemoglobin-albumin complex which has high stability of the oxygenated form, has high biocompatibility, and is easily prepared (synthesized), and an artificial plasma expander and an artificial oxygen carrier containing the complex are provided. The hemoglobin-albumin complex of the invention is characterized by having hemoglobin as the core, and albumin as the shell bound via a crosslinker to the above hemoglobin. Also, the artificial oxygen carrier of the invention is characterized by containing the hemoglobin-albumin complex of the invention.

10 Claims, 1 Drawing Sheet

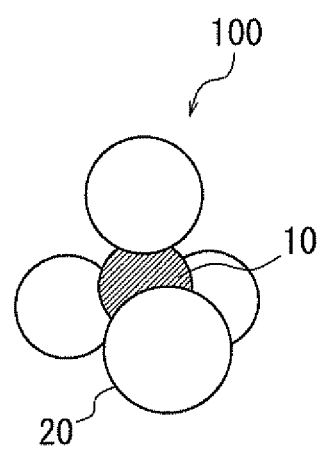

HEMOGLOBIN-ALBUMIN COMPLEX, AND ARTIFICIAL PLASMA EXPANDER AND ARTIFICIAL OXYGEN CARRIER CONTAINING THE COMPLEX

The present application is a 371 of PCT/JP2012/00118, filed Feb. 20, 2012.

BACKGROUND OF THE INVENTION

1. Field of the Invention

This invention relates to a hemoglobin-albumin complex, and an artificial plasma expander and an artificial oxygen carrier containing the complex, particularly to a hemoglobin-albumin complex (hererocluster) having hemoglobin and albumin bound via a crosslinker, and an artificial plasma expander and an artificial oxygen carrier containing the complex.

2. Related Art

One of the important roles of blood is oxygen transport. Oxygen is constantly supplied to body tissue cells by hemoglobin (hemeprotein having heme as the active center and a molecular weight of about 64,500) in a red blood cell contained in blood binding oxygen in the lung and dissociating oxygen in peripheral tissue.

When a large amount of bleeding from a human body occurs due to a disaster, accident or the like, oxygen transport within a body needs to be recovered/maintained by blood transfusion. In many medically advanced countries, the blood donation/transfusion system has been improved, and the risk involved in blood transfusion such as viral infection is considerably low.

However, when a red blood cell is administered, confirmation of blood type (crossmatching) needs to be done in advance. Also, the risk of being infected by an unknown virus cannot be completely eliminated. Moreover, since the storage period of a red blood cell is as short as 3 weeks at 4° C., the concern is that a sufficient amount of blood for transfusion cannot be ensured when a large scale disaster occurs. Furthermore, it is anticipated that in the future, along with declining birthrate and aging population, the population of blood donor generation decreases, and a stable supply of blood for transfusion becomes difficult to obtain.

In addition, currently, although development of substitutes for blood components other than a red blood cell (e.g., plasma protein) has progressed, development of an artificial red blood cell (oxygen carrier) as a substitute for a red blood cell has been delayed. Thus, if an artificial red blood cell (oxygen carrier) as a substitute for a red blood cell is developed, development of artificial blood would also be largely developed.

Under such a circumstance, development of an artificial oxygen carrier (artificial red blood cell) which has no blood type (is administrable to a human with any blood type), has no risk of viral infection and the like, is storable for a long period, and is usable anytime needed, has internationally been expanded.

However, in the United States, as an artificial oxygen carrier, the intramolecular crosslinked hemoglobin having hemoglobin intramolecular crosslinked (e.g., see Patent Document 1), the hemoglobin polymer having human hemoglobin bound via a crosslinker (e.g., see Patent Document 2), the hemoglobin polymer having bovine hemoglobin bound via a crosslinker (e.g., see Patent Document 3), the PEG hemoglobin having polyethylene glycol) (PEG) as a water soluble polymer bound to the molecular surface of human hemoglobin (e.g., see Patent Document 4), and the like have been developed, and the clinical studies have progressed. While these artificial oxygen carriers have a molecular design to avoid renal excretion due to disassociation to a subunit of hemoglobin and the like by crosslinking between subunits or increasing the molecular size (molecular weight), no formulation approved by Food and Drug Administration (FDA) and clinically used yet exists, for reasons that in the clinical study, a side effect such as increased blood pressure due to vasoconstriction occurs, no difference in effect is seen between the artificial oxygen carrier administration group and the saline administration group, and the like.

On the other hand, in Japan, development of a cellular type artificial oxygen carrier having hemoglobin encapsulated in the internal water phase of bilayer membrane vesicle (liposome) formed by self-organization of a phospholipid molecule in water has also progressed (e.g., see Patent Document 5). Although this cellular type artificial oxygen carrier does not have any problematic side effect and its practical application has been desired, it has not reached the clinical study, due to the problem that high preparation technology and initial cost are required.

Moreover, the inventors have focused on the multimolecular binding capacity of serum albumin contained in blood in a second larger amount to hemoglobin among protein, and developed an albumin-heme complex having iron porphyrin (heme) to be an oxygen binding site included in the hydrophobic pocket thereof (e.g., see Patent Document 6). Although it is clear that this albumin-heme complex has an oxygen binding capacity and an in vivo oxygen transport capacity, there are problems that the synthesis is complicated due to the special structure of a heme derivative, stability of the oxygenated form of a heme derivative is lower than stability of the oxygenated form of hemoglobin, and the like.

From the above background, development of a novel artificial oxygen carrier which has high stability of the oxygenated form, has high biocompatibility (e.g., no renal excretion, no side effect such as increased blood pressure), and is easily prepared (synthesized), has been strongly desired.

PRIOR ART DOCUMENTS

Patent Documents

Patent Document 1: JP-A-H10-306036
Patent Document 2: JP-A-H11-502821
Patent Document 3: JP-A-2006-516994
Patent Document 4: JP-A-2005-515225
Patent Document 5: JP-A-2004-307404
Patent Document 6: JP-A-H8-301873

SUMMARY OF THE INVENTION

Problem to be Solved by the Invention

The object of the invention is to provide a novel hemoglobin-albumin complex which has high stability of the oxygenated form, has high biocompatibility, and is easily prepared (synthesized), and an artificial plasma expander and an artificial oxygen carrier containing the complex.

Means for Solving the Problem

The inventors have discovered that the object can be achieved by cluster binding serum albumin having a negative surface charge via a crosslinker to the core comprising hemoglobin having an oxygen binding capacity.

More specifically, the hemoglobin-albumin complex of the invention is characterized by having hemoglobin as the core, and albumin as the shell bound via a crosslinker to the hemoglobin.

In the hemoglobin-albumin complex of the invention, the binding site to the crosslinker in the hemoglobin is desirably lysine.

In the hemoglobin-albumin complex of the invention, the binding site to the crosslinker in the albumin is desirably cysteine 34.

In the hemoglobin-albumin complex of the invention, the bond between the hemoglobin and the crosslinker is desirably an amide bond, and the bond between the albumin and the crosslinker is desirably any of a disulfide bond and a sulfide bond.

In the hemoglobin-albumin complex of the invention, the number of the albumin is desirably 1 to 7.

In the hemoglobin-albumin complex of the invention, the hemoglobin is desirably at least one kind selected from the group consisting of human hemoglobin, bovine hemoglobin, recombinant human hemoglobin, and intramolecular crosslinked hemoglobin.

In the hemoglobin-albumin complex of the invention, the albumin is desirably at least one kind selected from the group consisting of human serum albumin, bovine serum albumin, and recombinant human serum albumin.

In the hemoglobin-albumin complex of the invention, the crosslinker is desirably at least one kind selected from the group consisting of compounds represented by the following general formulae (1) to (3) and chemical formula (1).

[Chemical Formula 1]

General Formula (1)

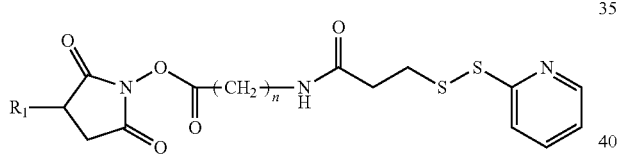

In the general formula (1), $R_1$ represents any of a hydrogen atom and $SO_3^- Na^+$, and n represents an integer of 1 to 10.

[Chemical Formula 2]

Chemical Formula (1)

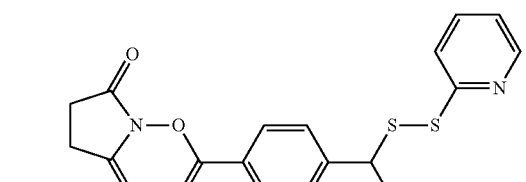

[Chemical Formula 3]

General Formula (2)

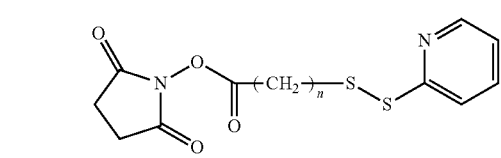

In the general formula (2), n represents an integer of 1 to 10.

[Chemical Formula 4]

General Formula (3)

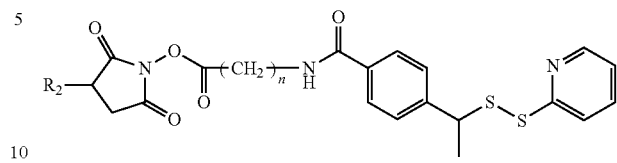

In the general formula (3), $R_2$ represents any of a hydrogen atom and $SO_3^- Na^+$, and n represents an integer of 1 to 10.

In the hemoglobin-albumin complex of the invention, the crosslinker is desirably at least one kind selected from the group consisting of compounds represented by the following general formula (4).

[Chemical Formula 5]

General Formula (4)

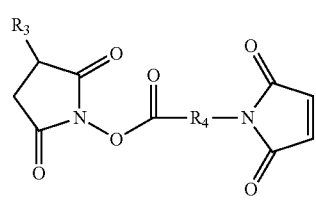

In the general formula (4), $R_3$ represents any of a hydrogen atom and $SO_3^- Na^+$, and $R_4$ represents any of the following general formulae (5) to (6) and the following chemical formulae (2) to (4).

[Chemical Formula 6]

General Formula (5)

In the general formula (5), n represents an integer of 1 to 10.

[Chemical Formula 7]

Chemical Formula (2)

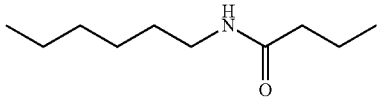

[Chemical Formula 8]

Chemical Formula (3)

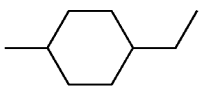

[Chemical Formula 9]

General Formula (6)

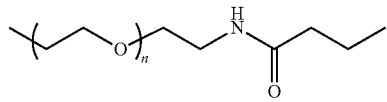

In the general formula (6), n represents an integer of 2, 4, 6, 8, 10 or 12.

[Chemical Formula 10]

Chemical Formula (4)

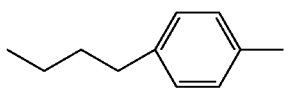

The artificial plasma expander of the invention is characterized by containing the hemoglobin-albumin complex of the invention.

The artificial oxygen carrier of the invention is characterized by containing the hemoglobin-albumin complex of the invention.

Effect of the Invention

According to the invention, it is possible to provide a novel hemoglobin-albumin complex which has high stability of the oxygenated form, has high biocompatibility, and is easily prepared (synthesized), and an artificial plasma expander and an artificial oxygen carrier containing the complex.

BRIEF DESCRIPTION OF DRAWINGS

The invention will be described with reference to the accompanying drawing, wherein:

FIG. 1 is a view showing one example of the hemoglobin-albumin complex of the invention.

MODE FOR CARRYING OUT THE INVENTION

Below, the invention will specifically be described with reference to the drawing if necessary.

(Hemoglobin-Albumin Complex)

The hemoglobin-albumin complex of the invention has at least hemoglobin as the core and albumin as the shell, and further has other sites if necessary.

The above hemoglobin and the above albumin are bound via a crosslinker.

For example, as shown in FIG. 1, the hemoglobin-albumin complex (star-shaped heterocluster) 100 of the invention has hemoglobin 10 as the core, and four albumin 20 as the shell. In FIG. 1, hemoglobin 10 and albumin 20 are bound via a crosslinker (not shown).

<Hemoglobin>

The above hemoglobin has a molecular weight of about 64500.

The above hemoglobin molecule is consisted of four subunits, and each subunit has one protoheme each. Oxygen is bound to an iron atom within the protoheme. More specifically, four oxygen molecules are bound to one hemoglobin molecule.

The above hemoglobin is not particularly limited as long as it is from vertebrate including human, can be selected accordingly depending on the object, and includes human hemoglobin, bovine hemoglobin, recombinant human hemoglobin, intramolecular crosslinked hemoglobin, and the like, for example. These may be used as one kind alone, or in combination of two kinds or more.

Among these, human hemoglobin is preferable in terms of high biocompatibility.

In addition, the above hemoglobin can be easily produced by protein synthesis (culturing).

—Human Hemoglobin—

The above human hemoglobin is not particularly limited as long as it is purified from a red blood cell derived from a human, and can be selected accordingly depending on the object.

—Bovine Hemoglobin—

The above bovine hemoglobin is not particularly limited as long as it is purified from a red blood cell derived from a bovine, and can be selected accordingly depending on the object.

—Recombinant Human Hemoglobin—

The above recombinant human hemoglobin is not particularly limited as long as it is produced from a normal gene recombination operation, culturing operation, and can be selected accordingly depending on the object.

—Intramolecular Crosslinked Hemoglobin—

The above intramolecular crosslinked hemoglobin is not particularly limited, can be selected accordingly depending on the object, and includes hemoglobin wherein subunits are bound via a crosslinker to each other, and the like, for example.

Specific examples of the above intramolecular crosslinked hemoglobin are not particularly limited, can be selected accordingly depending on the object, and include Diaspirin crosslinked hemoglobin (substance name: DCLHb, Baxter Healthcare Corporation), and the like, for example.

<Albumin>

The above albumin is a simple protein having a colloid osmotic pressure adjustment as a main role in blood, but also functions as transport protein for a nutritive substance or its metabolic product (e.g., fatty acid), a drug, or the like, and other than that, has pH buffering action, esterase activity, and the like. Moreover, the above albumin is, since it is plasma protein, remarkably advantageous regarding application to an organism, particularly use as a red blood cell substitute.

Since the isoelectric point of the above albumin is lower than 7, and under the physiological condition, the molecular surface is strongly negatively charged, it is difficult to leak out from a blood vessel due to electrostatic repulsion against a basal membrane (negatively charged) outside a vascular endothelial cell.

In addition, the above albumin can be easily produced by protein synthesis (culturing).

Although the number of albumin bound via a crosslinker to the above hemoglobin is not particularly limited and can be selected accordingly depending on the object, it is preferably 1 to 7. With not less than 7, binding is considered to be difficult due to steric hindrance.

A method for measuring the number of the above albumin is not particularly limited, can be selected accordingly depending on the object, and includes (1) a method of calculating based on the molecular weight of the entire hemoglobin-albumin complex measured by an electrophoresis method, the molecular weight of hemoglobin (64500), and the molecular weight of albumin (66500), (2) a method of calculating based on the concentration of protein calculated by the quantification of protein using a cyanomethemoglobin method (e.g., Alfresa Pharma Corporation, Ness Coat Hemo Kit N, No. 138016-14), and the concentration of hemoglobin calculated by the quantification of heme using a 660 nm method (e.g., Pierce Corporation, 660 nm Protein Assay Kit, No. 22662), (3) a method of observing with an electron microscope, and the like, for example.

Moreover, a method for isolating a hemoglobin-albumin complex with the predetermined number of albumin from a mixture of hemoglobin-albumin complexes with the different numbers of albumin is not particularly limited, can be selected accordingly depending on the object, and includes an isolation method by column chromatography, and the like, for example.

The above albumin is not particularly limited, can be selected accordingly depending on the object, and includes human serum albumin, bovine serum albumin, recombinant human serum albumin, and the like, for example.

—Human Serum Albumin—

The above human serum albumin is not particularly limited as long as it is purified from plasma protein derived from a human, and can be selected accordingly depending on the object.

The above human serum albumin is a simple protein (66500 Da) making up about 60% of plasma protein, and in blood, plays a role of maintaining colloid osmotic pressure and a role of storing or carrying various endogenous/exogenous substances. Since the isoelectric point of the above human serum albumin is as low as 4.8, and under the physiological condition, the molecular surface is strongly negatively charged, it is difficult to leak out from a blood vessel due to electrostatic repulsion against a basal membrane (negatively charged) outside a vascular endothelial cell.

—Bovine Serum Albumin—

The above bovine serum albumin is not particularly limited as long as it is purified from plasma protein derived from a bovine, and can be selected accordingly depending on the object.

—Recombinant Human Serum Albumin—

The above recombinant human serum albumin is not particularly limited as long as it is produced from a normal gene recombination operation, culturing operation, and can be selected accordingly depending on the object.

Additionally, in recent years in Japan, ahead of the world, the mass production system of recombinant human serum albumin having Pichia yeast as a host has been established, and the clinical use has started.

<Crosslinker>

The above crosslinker is not particularly limited as long as it is a difunctional crosslinker capable of linking hemoglobin and albumin, can be selected accordingly depending on the object, and includes compounds represented by the following general formulae (1) to (4) and chemical formula (1), and the like, for example. These may be used as one kind alone, or in combination of two kinds or more.

Among these, α-(N-succinimidyl)-ω-pyridyldithio crosslinker (in the following general formula (1), $R_1$ is a hydrogen atom, and n is 5), α-(N-succinimidyl)-ω-maleimide crosslinker (in the following general formula (4), $R_3$ is a hydrogen atom, and $R_4$ is the general formula (5), or $R_3$ is a hydrogen atom, $R_4$ is the general formula (5), and n=5, or moreover, $R_3$ is a hydrogen atom, and $R_4$ is the chemical formula (3)) are preferable.

[Chemical Formula 11]

General Formula (1)

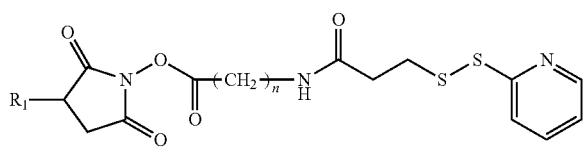

In the general formula (1), $R_1$ represents any of a hydrogen atom and $SO_3^- Na^+$, and n represents an integer of 1 to 10. For example, the one wherein n=5, and the like are generally included.

[Chemical Formula 12]

Chemical Formula (1)

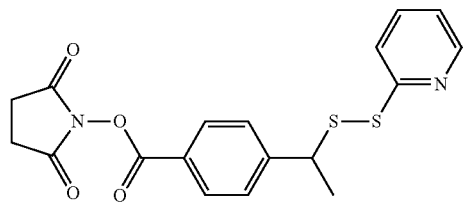

[Chemical Formula 13]

General Formula (2)

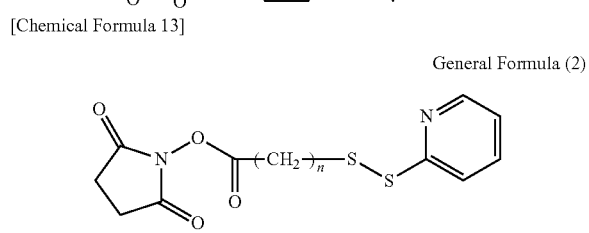

In the general formula (2), n represents an integer of 1 to 10. For example, the one wherein n=2, and the like are generally included.

[Chemical Formula 14]

General Formula (3)

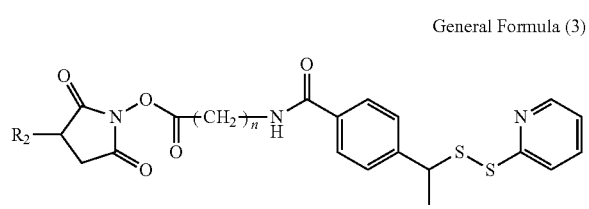

In the general formula (3), $R_2$ represents any of a hydrogen atom and $SO_3^- Na^+$, and n represents an integer of 1 to 10. For example, the one wherein n=5, and the like are generally included.

[Chemical Formula 15]

General Formula (4)

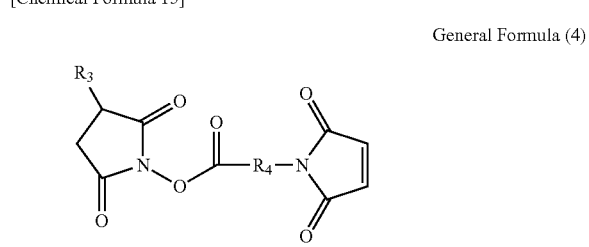

In the general formula (4), $R_3$ represents any of a hydrogen atom and $SO_3^- Na^+$, and $R_4$ represents any of the following general formulae (5) to (6) and the following chemical formulae (2) to (4).

[Chemical Formula 16]

General Formula (5)

$$-(CH_2)_n-$$

In the general formula (5), n represents an integer of 1 to 10.

[Chemical Formula 17]

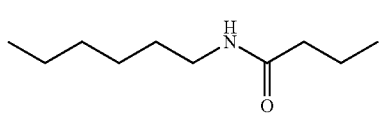

Chemical Formula (2)

[Chemical Formula 18]

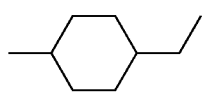

Chemical Formula (3)

[Chemical Formula 19]

General Formula (6)

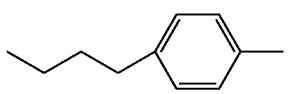

In the general formula (6), n represents an integer of 2, 4, 6, 8, 10 or 12.

[Chemical Formula 20]

Chemical Formula (4)

A succinimidyl group in the above crosslinker and an amino group (—$NH_2$) of the lysine residue in hemoglobin form an amide bond (covalent bond).

A method for forming the above amide bond includes stirring hemoglobin and a crosslinker at 5° C. to 30° C. for 0.2 hour to 3 hours, and the like, for example.

A pyridyldithio group (SS bond) in the above crosslinker and cysteine 34 (reduced type cysteine) in an albumin molecule form a disulfide bond (covalent bond). In addition, the disulfide bond has a characteristic of being easily broken.

A method for forming the above disulfide bond includes stirring albumin and a crosslinker at 5° C. to 30° C. for 1 hour to 40 hours, and the like, for example.

A maleimide group in the above crosslinker and cysteine 34 (reduced type cysteine) in an albumin molecule form a sulfide bond (covalent bond).

A method for forming the above sulfide bond includes stirring albumin and a crosslinker at 5° C. to 30° C. for 1 hour to 40 hours, and the like, for example.

Since only one cysteine 34 (reduced type cysteine) exists in an albumin molecule, the hemoglobin-albumin complex of the invention becomes a star-shaped cluster structure (e.g., FIG. 1), and the molecular structure is clear.

<Other Sites>

The above other sites are particularly limited, can be selected accordingly depending on the object, and includes poly(ethylene glycol) introduced to the albumin surface by a covalent bond, protein bound to hemoglobin along with albumin, and the like, for example.

Although the isoelectric point of the hemoglobin-albumin complex of the invention is not particularly limited and can be adjusted accordingly depending on the object, it is preferably 4.7 to 6.5, and more preferably 4.7 to 5.5.

From above, the hemoglobin-albumin complex of the invention is, since the oxygen binding site is hemoglobin, capable of forming a stable oxygenated form, and supplying oxygen efficiently to body tissue. Also, the hemoglobin-albumin complex of the invention, since albumin covers around the core hemoglobin, has the isoelectric point as low as albumin, and does not cause renal excretion, leakage from a vascular endothelial cell, or increased blood pressure due to vasoconstriction. Moreover, hemoglobin and albumin, which are living substances, are thought to have high metabolism. Furthermore, the hemoglobin-albumin complex of the invention, despite relatively easy preparation, has a clear three dimensional structure.

In addition, the hemoglobin-albumin complex of the invention of the present application is, by having hemoglobin as the oxygen binding site to have the oxygen binding dissociation curve as an S curve, predicted to have an effect that the oxygen carrying ability improves, particularly when the oxygen partial pressure of a peripheral cell decreases.

From above, the hemoglobin-albumin complex of the invention can be recognized as an incomparable artificial oxygen carrier having safety (biocompatibility) and efficacy at the same time.

(Artificial Plasma Expander)

The artificial plasma expander of the invention is characterized by containing the hemoglobin-albumin complex of the invention. In addition, the above artificial plasma expander is a transfusion or a transfusion preparation to be administered to a patient lacking the amount of circulating blood due to bleeding and the like, for the purpose of recovering/maintaining the amount of circulating blood.

(Artificial Oxygen Carrier)

The artificial oxygen carrier of the invention is characterized by containing the hemoglobin-albumin complex of the invention. In addition, the above artificial oxygen carrier is a substance capable of carrying an oxygen molecule, and functions as a substitute for a red blood cell when administered to an organism.

EXAMPLES

Below, the invention will specifically be described based on Examples, but the invention is not limited to these Examples.

Example 1

Preparation Example 1

Preparation of Mercapto Human Serum Albumin (HSA-SH)

In order to reduce all residues of cysteine (Cys-34) in human serum albumin (HSA) having the mercapto fraction as low as about 25% into thiol groups, the following operation was carried out.

Firstly, to a sample bottle (30 mL volume), it was charged by 1.3 mL of human serum albumin (920 μM), and diluted with 10.7 mL of phosphate buffered saline solution (PBS, 10 mM, pH 7.4) to prepare 0.1 mM (12 mL) of human serum albumin solution.

Next, to an Eppendorf tube (2 mL volume), it was charged by 12.3 mg of dithiothreitol (DTT, manufactured by Wako Pure Chemical Industries, Ltd.), lightly deaerated, then added with 1 mL of separately deaerated phosphate buffered saline solution (PBS) and dissolved to prepare 1 mL of dithiothreitol (DTT) solution (80 mL).

To human serum albumin solution (12 mL), it was added with 30 μL of dithiothreitol (DTT) solution (dithiothreitol/ human serum albumin (DTT/HSA)=2 (mol/mol)), shaken well, and allowed to stand at room temperature for 40 minutes.

12.0 mL of that solution was dispensed into a few centrifugal concentrators (manufactured by Sartorius Stedim Biotech SA, VIVA SPIN 20, ultrafiltration molecular weight 5 kDa), each was diluted with phosphate buffered saline solution (PBS, 10 mM, pH 7.4), and concentrated to about 1.0 mL under conditions of at 4000 rpm, for 30 minutes and at 4° C. using a centrifugal separator (manufactured by Beckman Coulter Inc., Allegra X-15R Centrifuge).

Moreover, it was added to with 19 mL of phosphate buffered saline solution (PBS), and concentrated to about 1.0 mL under the same conditions.

By repeating this dilution/concentration operation three times, excessive dithiothreitol (DTT) could be removed.

Lastly, samples in a few tubes were collected in a sample bottle (8 mL volume) and the total volume was adjusted with phosphate buffered saline solution (PBS) to 2.4 mL, and as a result, the mercapto human serum albumin (HSA-SH) concentration became 0.5 mM.

By using the exchange reaction of a thiol group and a disulfide bond, the mercapto fraction of human serum albumin (HSA) was quantified. Since 2,2'-dithiopyridine (2,2'-DTP) reacts with a free thiol (SH) group to generate 2-thiopyridinone (2-TP), by adding 2,2'-dithiopyridine (2,2'-DTP) to human serum albumin (HSA) and measuring the amount of generated 2-thiopyridinone (2-TP), the amount of thiol (SH) group in cysteine 34 (Cys-34) could be quantified.

To an Eppendorf tube (2 mL volume), it was charged by 2.2 mg of 2,2'-dithiopyridine (2,2'-DTP), added with 1 mL of phosphate buffered saline solution (PBS) and shaken well to prepare 1 mL of 2,2'-dithiopyridine (2,2'-DTP) solution (10 mM).

Firstly, to a quartz cell (1 cm) for spectroscopy, 2.7 mL of phosphate buffered saline solution (PBS) was added, and ultraviolet visible absorption (UV-Vis.) spectrum (190 nm-700 nm) was measured using an ultraviolet visible spectrometer (trade name: ultraviolet visible spectrometer 8454, manufactured by Agilent Technologies Inc.) (blank).

Next, to the quartz cell, 0.3 mL of mercapto human serum albumin (HSA-SH) (500 µM) was added and shaken well (It became a 10 times dilution. Human serum albumin (HSA) concentration=50 µM), and ultraviolet visible absorption spectrum measurement was carried out.

Then, 0.075 mL of 2,2'-dithiopyridine (2,2'-DTP) solution (10 mM) (dithiopyridine/human serum albumin (DTP/HSA)=5 (mol/mol)) was added to and shaken well.

After allowing it to stand for 30 minutes, ultraviolet visible absorption spectrum measurement was carried out. From the absorbance of 342 nm and the molar absorbance coefficient of 2-thiopyridinone (2-TP) ($\epsilon_{342}$=8.1×10$^3$ M$^{-1}$ cm$^{-1}$), the concentration of a pyridyldithio group was calculated. When it was divided by the human serum albumin (HSA) concentration to calculate the mercapto fraction (percentage of the reduced type cysteine 34) in the human serum albumin (HSA), it was about 80% to 100%.

Preparation Example 2

Preparation of Human Hemoglobin-Crosslinker Conjugate (Hb-SPDPH)

To a sample bottle (8 mL volume), it was charged by 0.39 mL of human CO hemoglobin (Hb) solution (509 µM), and diluted with 1.61 mL of phosphate buffered saline solution (PBS) to be 0.1 mM 2 mL.

Next, to an Eppendorf tube (2 mL volume), it was charged by 2.1 mg of succinimidyl-6[3-(2-pyridyldithio)propionamido]hexanoate (SPDPH, manufactured by Pierce Corporation), added with 0.25 mL of ethanol (EtOH) and dissolved to prepare 20 mM ethanol solution of succinimidyl-6[3-(2-pyridyldithio)propionamido]hexanoate (SPDPH).

To the above human hemoglobin (Hb) solution (2 mL), it was added with 0.2 mL of succinimidyl-6[3-(2-pyridyldithio) propionamido]hexanoate (SPDPH) solution (succinimidyl-6 [3-(2-pyridyldithio)propionamido]hexanoate/human hemoglobin (SPDPH/Hb)=18 (mol/mol)), while stirring (100 rpm), and stirred at room temperature for 30 minutes.

From the resultant reaction solution, unreacted succinimidyl-6[3-(2-pyridyldithio)propionamido]hexanoate (SPDPH) was removed by the method described in Preparation Example 1.

Specifically, 2.2 mL of human hemoglobin (Hb) solution was moved to a centrifugal concentrator (Vivaspin 20), diluted with about 18 mL of phosphate buffered saline solution (PBS) to ten times, and then concentrated to about 1.0 mL under conditions of at 4000 rpm, for 30 minutes and at 4° C.

To that, it was added with 19 mL of phosphate buffered saline solution (PBS), and concentrated to about 1.0 mL under the same conditions.

By repeating this dilution/concentration operation a few times, unreacted succinimidyl-6[3-(2-pyridyldithio)propionamido]hexanoate (SPDPH) can be removed.

Lastly, a sample in a tube was moved to a sample bottle (8 mL volume), and phosphate buffered saline solution (PBS) was added to adjust the total volume to 2.0 mL.

The human hemoglobin-crosslinker conjugate (Hb-SPDPH) concentration becomes 0.1 mM.

The number of pyridyldithio groups introduced to the human hemoglobin-crosslinker conjugate (Hb-SPDPH) molecular surface can be determined by reducing the terminal disulfide bond with dithiothreitol (DTT) and measuring the amount of free 2-thiopyridinone (2TP).

To an Eppendorf tube (2 mL volume), it was charged by 12.3 mg of dithiothreitol (DTT), lightly deaerated, then added with 1 mL of separately deaerated phosphate buffered saline solution (PBS) and dissolved to prepare 1 mL of dithiothreitol (DTT) solution (80 mL).

To a quartz cell (1 cm×1 cm) for spectroscopy, 2.85 mL of phosphate buffered saline solution (PBS) was added, and ultraviolet visible absorption (UV-Vis.) spectrum (190 nm-700 nm) was measured (blank).

Next, 0.15 mL of human hemoglobin-crosslinker conjugate (Hb-SPDPH, 100 µM) was added and shaken well (It became a 20 times dilution. Human hemoglobin (Hb) concentration=5 µM), and ultraviolet visible absorption spectrum was measured.

Then, 18 µL, of dithiothreitol (DTT) solution (80 mM) was added (dithiothreitol/human hemoglobin (DTT/Hb)=95 (mol/mol)), and shaken well.

After allowing it to stand for 30 minutes, ultraviolet visible spectrum was measured at 190 nm to 700 nm. From the absorbance of 342 nm and the molar absorbance coefficient of 2-thiopyridinone (2-TP) ($\epsilon_{342}$=8.1×10$^3$ M$^{-1}$cm$^{-1}$) values, the concentration of pyridyldithio groups was calculated.

When the number of pyridyldithio groups per molecule of human hemoglobin was determined from the ratio to the human hemoglobin (Hb) concentration, it was 8 to 9.

Preparation Example 3

Preparation of Human Hemoglobin/Human Serum Albumin (Hb/HSA$_n$) Heterocluster

To a sample bottle (8 mL volume), it was charged by 2 mL of mercapto human serum albumin (HSA-SH) (500 µM)

obtained in Preparation Example 1, slowly added dropwise with 1 mL of human hemoglobin-crosslinker conjugate (Hb-SPDPH) obtained in Preparation Example 2, while stirring (100 rpm) with a stirrer, and reacted at room temperature under shading for 20 hours.

The reaction solution (3 mL) was filtered through a DISMIC filter (diameter 0.45 μm, manufactured by Advantec, Ltd.), and 2 mL of the obtained mixture was separated/purified at 4° C. using a low pressure chromatography system (GE Healthcare, AKTA prime plus, column: Superdex G200 10/300 GL, eluate: phosphate buffered saline solution (PBS)). The eluate was collected by a fraction collector. In the elution curve, a plurality of peaks appeared earlier than peaks of human hemoglobin (Mw: 64.5 kDa) or human serum albumin (Mw: 66.5 kDa) suggesting generation of the high molecular weight form. When Native-PAGE electrophoresis measurement (Wako Pure Chemical, SuperSep Ace 5-12% 13 well) was carried out on a fraction containing four main peaks, a clear band appeared around Mw: 180 kDa, 260 kDa, 360 kDa, and 470 kDa, so each fraction containing each component only was isolated and collected.

For the isolated high molecular weight form, the human hemoglobin concentration was quantified by a cyanomethemoglobin method (Alfresa Pharma Corporation, Ness Coat Hemo Kit N, No. 138016-14), and the protein concentration was quantified by a 660 nm method (Pierce Corporation, 660 nm Protein Assay Kit, No. 22662).

It was clear that from the low molecular weight components, heteroclusters ((Hb/HSA$_1$) SPDPH, (Hb/HSA$_2$) SPDPH, (Hb/HSA$_3$) SPDPH, and (Hb/HSA$_4$) SPDPH) having 1, 2, 3 and 4 human serum albumin bound to human hemoglobin, and having the human serum albumin/human hemoglobin ratio to be 1.1, 2.2, 3.0 and 3.8, were generated.

Example 2

A human hemoglobin-crosslinker conjugate (Hb-SSPDPH) was prepared according to the same method as Preparation Examples 1 and 2 in Example 1, except for using sulfosuccinimidyl-6[3-(2-pyridyldithio)propionamido]hexanoate (SSPDPH, manufactured by Pierce Corporation) instead of succinimidyl-6[3-(2-pyridyldithio)propionamido] hexanoate (SPDPH, manufactured by Pierce Corporation) in Preparation 2 in Example 1. When the concentration of pyridyldithio groups was calculated, and the number of pyridyldithio groups per molecule of human hemoglobin was determined from the ratio to the human hemoglobin (Hb) concentration, it was 7 to 8.

Subsequently, according to the same method as Preparation Example 3 in Example 1, except for using the human hemoglobin-crosslinker conjugate (Hb-SSPDPH) instead of the human hemoglobin-crosslinker conjugate (Hb-SPDPH) in Preparation Example 3 in Example 1, heteroclusters ((Hb/HSA$_1$) SSPDPH, (Hb/HSA$_2$) SSPDPH, (Hb/HSA$_3$) SSPDPH, and (Hb/HSA$_4$) SSPDPH) having 1, 2, 3 and 4 human serum albumin bound to human hemoglobin were synthesized and each isolated.

Example 3

A human hemoglobin-crosslinker conjugate (Hb-SMPT) was prepared according to the same method as Preparation Examples 1 and 2 in Example 1, except for using 4-succinimidyloxycarbonyl-methyl-α(2-pyridyldithio)toluene) (SMPT, manufactured by Pierce Corporation) instead of succinimidyl-6[3-(2-pyridyldithio)propionamido]hexanoate (SPDPH, manufactured by Pierce Corporation) in Preparation Example 2 in Example 1. When the concentration of pyridyldithio groups was calculated, and the number of pyridyldithio groups per molecule of human hemoglobin was determined from the ratio to the human hemoglobin (Hb) concentration, it was 7 to 9.

Subsequently, according to the same method as Preparation Example 3 in Example 1, except for using the human hemoglobin-crosslinker conjugate (Hb-SMPT) instead of the human hemoglobin-crosslinker conjugate (Hb-SPDPH) in Preparation Example 3 in Example 1, heteroclusters ((Hb/HSA$_1$) SMPT, (Hb/HSA$_2$) SMPT, (Hb/HSA$_3$) SMPT, and (Hb/HSA$_4$) SMPT) having 1, 2, 3 and 4 human serum albumin bound to human hemoglobin were synthesized and each isolated.

Example 4

A human hemoglobin-crosslinker conjugate (Hb-SPDP) was prepared according to the same method as Preparation Examples 1 and 2 in Example 1, except for using succinimidyl-3-(2-pyridyldithio)propionate (SPDP, manufactured by Pierce Corporation) instead of succinimidyl-6[3-(2-pyridyldithio)propionamido]hexanoate (SPDPH, manufactured by Pierce Corporation) in Preparation Example 2 in Example 1.

When the concentration of pyridyldithio groups was calculated, and the number of pyridyldithio groups per molecule of human hemoglobin was determined from the ratio to the Hb concentration, it was 8 to 9.

Subsequently, according to the same method as Preparation Example 3 in Example 1, except for using the human hemoglobin-crosslinker conjugate (Hb-SPDP) instead of the human hemoglobin-crosslinker conjugate (Hb-SPDPH) in Preparation Example 3 in Example 1, heteroclusters ((Hb/HSA$_1$) SPDP, (Hb/HSA$_2$) SPDP, (Hb/HSA$_3$) SPDP, and (Hb/HSA$_4$) SPDP) having 1, 2, 3 and 4 human serum albumin bound to human hemoglobin were synthesized and each isolated.

Example 5

A human hemoglobin-crosslinker conjugate (Hb-SSMPTH) was prepared according to the same method as Preparation Examples 1 and 2 in Example 1, except for using sulfosuccinimidyl-6-[α-methyl-α-(2-pyridyldithio)toluamido)hexanoate (SSMPTH, manufactured by Pierce Corporation) instead of succinimidyl-6[3-(2-pyridyldithio)propionamido]hexanoate (SPDPH, manufactured by Pierce Corporation) in Preparation Example 2 in Example 1. When the concentration of pyridyldithio groups was calculated, and the number of pyridyldithio groups per molecule of human hemoglobin was determined from the ratio to the Hb concentration, it was 7 to 8.

Subsequently, according to the same method as Preparation Example 3 in Example 1, except for using the human hemoglobin-crosslinker conjugate (Hb-SSMPTH) instead of the human hemoglobin-crosslinker conjugate (Hb-SPDPH) in Preparation Example 3 in Example 1, heteroclusters ((Hb/HSA$_1$) SSMPTH, (Hb/HSA$_2$) SSMPTH, (Hb/HSA$_3$) SSMPTH, and (Hb/HSA$_4$) SSMPTH) having 1, 2, 3 and 4 human serum albumin bound to human hemoglobin were synthesized and each isolated.

Example 6

Preparation Example 1

Preparation of Human Hemoglobin-Crosslinker Conjugate (Hb-SMPH)

To a sample bottle (8 mL volume), it was charged by 0.39 mL of human CO hemoglobin (Hb) solution (509 μM), and diluted with 1.61 mL of phosphate buffered saline solution (PBS) to be 0.1 mM 2 mL. Next, 7.6 mg of succinimidyl-6-(β-maleimidopropionamido)hexanoate (SMPH, manufactured by Pierce Corporation) was dissolved in 0.25 mL of dimethyl sulfoxide (DMSO) to prepare 80 mM dimethyl sulfoxide (DMSO) solution of succinimidyl-6-(β-maleimidopropionamido)hexanoate (SMPH). To the above human hemoglobin (Hb) solution (2 mL), it was added with 0.047 mL of succinimidyl-6-(β-maleimidopropionamido)hexanoate (SMPH) solution (succinimidyl-6-(β-maleimidopropionamido)hexanoate/human hemoglobin (SMPH/Hb) =18 (mol/mol)), while stirring (100 rpm), and stirred at room temperature for 30 minutes. From the resultant reaction solution, unreacted succinimidyl-6-(β-maleimidopropionamido)hexanoate (SMPH) was removed by the same method as the method described in Preparation Example 2 in Example 1. Specifically, 2.1 mL of human hemoglobin (Hb) solution was moved to a centrifugal concentrator (Vivaspin 20), diluted with about 18 mL of phosphate buffered saline solution (PBS) to ten times, and then concentrated to about 1.0 mL (1/10) at 4000 rpm, for 30 minutes and at 4° C. To that, it was added with 19 mL of phosphate buffered saline solution (PBS), and concentrated to about 1.0 mL under the same conditions. By repeating this dilution/concentration operation three times, unreacted succinimidyl-6-(β-maleimidopropionamido)hexanoate (SMPH) was removed. Lastly, a sample in a tube was moved to a sample bottle (8 mL volume), and the total volume was adjusted with phosphate buffered saline solution (PBS) to 2.0 mL. The human hemoglobin-crosslinker conjugate (Hb-SMPH) concentration became 0.1 mM.

Preparation Example 2

Human Hemoglobin/Human Serum Albumin (Hb/HSA$_n$) Heterocluster

To a sample bottle (8 mL volume), it was charged by 2 mL of mercapto human serum albumin (HSA-SH) (500 μM) obtained in Preparation Example 1 in Example 1, slowly added dropwise with 1 mL of human hemoglobin-crosslinker conjugate (Hb-SMPH), while stirring (100 rpm) with a stirrer, and reacted at room temperature under shading for 20 hours.

The reaction solution (3 mL) was filtered through a DISMIC filter (diameter 0.45 μm, manufactured by Advantec, Ltd.), and 2 mL of the resultant mixture was separated/purified at 4° C., using a low pressure chromatography system (GE Healthcare, AKTA prime plus, column: Superdex G200 10/300 GL, eluate: phosphate buffered saline solution (PBS)). The eluate was collected by a fraction collector. In the elution curve, a plurality of peaks appeared earlier than peaks of human hemoglobin (Mw: 64.5 kDa) or human serum albumin (Mw: 66.5 kDa) suggesting generation of the high molecular weight form. When Native-PAGE electrophoresis measurement (Wako Pure Chemical, SuperSep Ace 5-12% 13 well) was carried out on a fraction containing four main peaks, a clear band appeared around Mw: 180 kDa, 260 kDa, 360 kDa and 470 kDa, so each fraction containing each component only was isolated and collected.

For the isolated high molecular weight form, the human hemoglobin concentration was quantified by a cyanomethemoglobin method (Alfresa Pharma Corporation, Ness Coat Hemo Kit N, No. 138016-14), and the protein concentration was quantified by a 660 nm method (Pierce Corporation, 660 nm Protein Assay Kit, No. 22662). It was clear that from the low molecular weight components, heteroclusters ((Hb/HSA$_1$) SMPH, (Hb/HSA$_2$) SMPH, (Hb/HSA$_3$) SMPH, and (Hb/HSA$_4$) SMPH) having 1, 2, 3 and 4 human serum albumin bound to human hemoglobin, and having the human serum albumin/human hemoglobin ratio to be 1.2, 2.3, 3.3 and 3.9, were synthesized.

Example 7

A human hemoglobin-crosslinker conjugate (Hb-MAS) was prepared according to the same method as Preparation Example 1 in Example 6, except for using (α-maleimidoacetoxy)succinimide ester (MAS, manufactured by Pierce Corporation) instead of succinimidyl-6-(β-maleimidopropionamido)hexanoate (SMPH, manufactured by Pierce Corporation) in Preparation Example 1 in Example 6.

According to the same method as Preparation Example 2 in Example 6, except for using the human hemoglobin-crosslinker conjugate (Hb-MAS) instead of the human hemoglobin-crosslinker conjugate (Hb-SMPH) in Preparation Example 2 in Example 6, heteroclusters ((Hb/HSA$_1$) MAS, (Hb/HSA$_2$) MAS, (Hb/HSA$_3$) MAS, and (Hb/HSA$_4$) MAS) having 1, 2, 3 and 4 human serum albumin bound to human hemoglobin were synthesized and isolated.

Example 8

A human hemoglobin-crosslinker conjugate (Hb-MCS) was prepared according to the same method as Preparation Example 1 in Example 6, except for using (ϵ-maleimidocaproyloxy)succinimide ester (MCS, manufactured by Pierce Corporation) instead of succinimidyl-6-(β-maleimidopropionamido)hexanoate (SMPH, manufactured by Pierce Corporation) in Preparation Example 1 in Example 6.

According to the same method as Preparation Example 2 in Example 6, except for using the human hemoglobin-crosslinker conjugate (Hb-MCS) instead of the human hemoglobin-crosslinker conjugate (Hb-SMPH) in Preparation Example 2 in Example 6, heteroclusters ((Hb/HSA$_1$) MCS, (Hb/HSA$_2$) MCS, (Hb/HSA$_3$) MCS, and (Hb/HSA$_4$) MCS) having 1, 2, 3 and 4 human serum albumin bound to human hemoglobin were synthesized and isolated.

Example 9

A human hemoglobin-crosslinker conjugate (Hb-MCSS) was prepared according to the same method as Preparation Example 1 in Example 6, except for using (ϵ-maleimidocaproyloxy)sulfosuccinimide ester (MCSS, manufactured by Pierce Corporation) instead of succinimidyl-6-(β-maleimidopropionamido)hexanoate (SMPH, manufactured by Pierce Corporation) in Preparation Example 1 in Example 6.

According to the same method as Preparation Example 2 in Example 6, except for using the human hemoglobin-crosslinker conjugate (Hb-MCSS) instead of the human hemoglobin-crosslinker conjugate (Hb-SMPH) in Preparation Example 2 in Example 6, heteroclusters ((Hb/HSA$_1$) MCSS, (Hb/HSA$_2$) MCSS, (Hb/HSA$_3$) MCSS, and (Hb/HSA$_4$) MCSS) having 1, 2, 3 and 4 human serum albumin bound to human hemoglobin were synthesized and isolated.

Example 10

A human hemoglobin-crosslinker conjugate (Hb-SMCC) was prepared according to the same method as Preparation Example 1 in Example 6, except for using succinimidyl-4-(N-maleimidomethyl)cyclohexane-1-carboxylate (SMCC, manufactured by Pierce Corporation) instead of succinimidyl-6-(β-maleimidopropionamido)hexanoate (SMPH, manufactured by Pierce Corporation) in Preparation Example 1 in Example 6.

According to the same method as Preparation Example 2 in Example 6, except for using the human hemoglobin-crosslinker conjugate (Hb-SMCC) instead of the human hemoglobin-crosslinker conjugate (Hb-SMPH) in Preparation Example 2 in Example 6, heteroclusters ((Hb/HSA$_1$) SMCC, (Hb/HSA$_2$) SMCC, (Hb/HSA$_3$) SMCC, and (Hb/HSA$_4$) SMCC) having 1, 2, 3 and 4 human serum albumin bound to human hemoglobin were synthesized and isolated.

Example 11

A human hemoglobin-crosslinker conjugate (Hb-SM(PEG)$_6$) was prepared according to the same method as Preparation Example 1 in Example 6, except for using succinimidyl-[(N-maleimidopropionamido)-6-ethyleneglycol] ester (SM(PEG)$_6$, manufactured by Pierce Corporation) instead of succinimidyl-6-(β-maleimidopropionamido)hexanoate (SMPH, manufactured by Pierce Corporation) in Preparation Example 1 in Example 6.

According to the same method as Preparation Example 2 in Example 6, except for using the human hemoglobin-crosslinker conjugate (Hb-SM(PEG)$_6$) instead of the human hemoglobin-crosslinker conjugate (Hb-SMPH) in Preparation Example 2 in Example 6, heteroclusters ((Hb/HSA$_1$) SM(PEG)$_6$, (Hb/HSA$_2$) SM(PEG)$_6$, (Hb/HSA$_3$) SM(PEG)$_6$, and (Hb/HSA$_4$) SM(PEG)$_6$) having 1, 2, 3 and 4 human serum albumin bound to human hemoglobin were synthesized, and isolated.

Example 12

A human hemoglobin-crosslinker conjugate (Hb-SMUS) was prepared according to the same method as Preparation Example 1 in Example 6, except for using κ-(maleimidoundecanoyloxy)sulfosuccinimide ester (SMUS, manufactured by Pierce Corporation) instead of succinimidyl-6-(β-maleimidopropionamido)hexanoate (SMPH, manufactured by Pierce Corporation) in Preparation Example 1 in Example 6.

According to the same method as Preparation Example 2 in Example 6, except for using the human hemoglobin-crosslinker conjugate (Hb-SMUS) instead of the human hemoglobin-crosslinker conjugate (Hb-SMPH) in Preparation Example 2 in Example 6, heteroclusters ((Hb/HSA$_1$) SMUS, (Hb/HSA$_2$) SMUS, (Hb/HSA$_3$) SMUS, and (Hb/HSA$_4$) SMUS) having 1, 2, 3 and 4 human serum albumin bound to human hemoglobin were synthesized and isolated.

Example 13

A bovine hemoglobin-crosslinker conjugate (BHb-SPDPH) was prepared according to the same method as Preparation Examples 1 and 2 in Example 1, except for using bovine hemoglobin (BHb) instead of human hemoglobin in Preparation Example 2 in Example 1. When the concentration of pyridyldithio groups was calculated, and the number of pyridyldithio groups per molecule of human hemoglobin was determined from the ratio to the bovine hemoglobin (BHb) concentration, it was 7 to 9.

Subsequently, according to the same method as Preparation Example 3 in Example 1, except for using the bovine hemoglobin-crosslinker conjugate (BHb-SPDPH) instead of the human hemoglobin-crosslinker conjugate (Hb-SPDPH) in Preparation Example 3 in Example 1, heteroclusters ((BHb/HSA$_1$) SPDPH, (BHb/HSA$_2$) SPDPH, (BHb/HSA$_3$) SPDPH, and (BHb/HSA$_4$) SPDPH) having 1, 2, 3 and 4 human serum albumin bound to bovine hemoglobin were synthesized and each isolated.

Example 14

A bovine hemoglobin-crosslinker conjugate (BHb-MCS) was prepared according to the same method, except for using bovine hemoglobin (BHb) instead of human hemoglobin in Example 8.

According to the same method, except for using the bovine hemoglobin-crosslinker conjugate (BHb-MCS) instead of the human hemoglobin-crosslinker conjugate (Hb-MCS) in Example 8, heteroclusters ((BHb/HSA$_1$) MCS, (BHb/HSA$_2$) MCS, (BHb/HSA$_3$) MCS, and (BHb/HSA$_4$) MCS) having 1, 2, 3 and 4 human serum albumin bound to bovine hemoglobin were synthesized and each isolated.

Example 15

A bovine hemoglobin-crosslinker conjugate (BHb-SMCC) was prepared according to the same method, except for using bovine hemoglobin (BHb) instead of human hemoglobin in Example 10.

According to the same method, except for using the bovine hemoglobin-crosslinker conjugate (BHb-SMCC) instead of the human hemoglobin-crosslinker conjugate (Hb-SMCC) in Example 10, heteroclusters ((BHb/HSA$_1$) SMCC, (BHb/HSA$_2$) SMCC, (BHb/HSA$_3$) SMCC, and (BHb/HSA$_4$) SMCC) having 1, 2, 3 and 4 human serum albumin bound to bovine hemoglobin were synthesized and each isolated.

—Isoelectric Point Electrophoresis Measurement—

When the isoelectric point electrophoreses (Invitrogen, NOVEX IEF gel) of the (human hemoglobin/human serum albumin) heteroclusters (Hb/HSA$_1$) SPDPH, (Hb/HSA$_2$) SPDPH, (Hb/HSA$_3$) SPDPH, and (Hb/HSA$_4$) SPDPH obtained in Example 1 were measured, the isoelectric points (pI values) of each herocluster were 5.1, 5.1, 5.2 and 5.3, and it was clear that they were substantially decreased as compared to human hemoglobin (pI=7.0). From that the pI value was decreased along with an increase in the number of human serum albumin bound, a structure of having human serum albumin bound to the human hemoglobin molecular surface was also shown.

In addition, the intramolecular crosslinked hemoglobin having hemoglobin intramolecular crosslinked, the hemoglobin polymer having human hemoglobin bound via a crosslinker, and the hemoglobin polymer having bovine hemoglobin bound via a crosslinker are all thought to have the isoelectric point around 7.0, and also the isoelectric point of the albumin-heme complex is 4.8.

—Oxygen Affinity (P$_{50}$) Measurement—

By substituting the phosphate buffered saline solution (PBS) of the human hemoglobin-human serum albumin herocluster ((Hb/HSA$_4$)SPDPH) obtained in Example 1 with nitrogen sufficiently to deoxygenate, and then adding sodium dithionate prepared separately under a nitrogen atmosphere, the heme iron of human hemoglobin was reduced.

Since the ultraviolet visible absorption spectrum of this phosphate buffered saline solution (PBS) showed $\lambda_{max}$: 430 nm, 557 nm and matched the spectrum pattern of the deoxygenated form (deoxy form) of human hemoglobin, it was clear that the human hemoglobin site of the human hemoglobin-human serum albumin herocluster ((Hb/HSA$_4$)SPDPH) formed the deoxy form having no oxygen bound.

Here, since by flowing oxygen, the spectrum of the oxygenated form (oxy form) was immediately obtained ($\lambda_{max}$:

412 nm, 540 nm, 575 nm), and by flowing nitrogen again, it became the spectrum pattern of the deoxy form, it was shown that the human hemoglobin-human serum albumin heterocluster ((Hb/HSA$_4$)SPDPH) reversibly adsorbed and desorbed oxygen.

On the other hand, by flowing carbon oxide, an extremely stable carbon oxide form ($\lambda_{max}$: 419 nm, 538 nm, 569 nm) was formed. When the oxygen affinity (P$_{50}$) (oxygen partial pressure when the oxygen binding rate is 50% in the oxygen binding dissociation curve graph) was calculated from the ultraviolet visible absorption spectral change to different oxygen partial pressures using Hill equation, P$_{50}$ of the human hemoglobin-human serum albumin heterocluster ((Hb/HSA$_4$)SPDPH) was 13 Torr (37° C.).

When the same experiment was carried out for the other human hemoglobin-human serum albumin heteroclusters ((Hb/HSA$_1$)SPDPH, (Hb/HSA$_2$)SPDPH, and (Hb/HSA$_3$)SPDPH), P$_{50}$ (37° C.) were 12 Torr (37° C.), 12 Torr (37° C.), and 11 Torr (37° C.), respectively.

Moreover, when the same experiment was carried out for the bovine hemoglobin-human serum albumin heteroclusters obtained in the Example 14 ((BHb/HSA$_1$)MCS, (BHb/HSA$_2$)MCS, (BHb/HSA$_3$)MCS, and (BHb/HSA$_4$)MCS), P$_{50}$ (37° C.) were 10 Torr (37° C.), 10 Torr (37° C.), 11 Torr (37° C.), and 12 Torr (37° C.), respectively.

Industrial Applicability

The artificial oxygen carrier having the hemoglobin-albumin complex of the invention as an active component can be used as a highly safe transfusion substitute even when administered to an organism. In addition, it can also be used as a stock solution for a replacement organ or tissue, a culture solution for regenerated tissue, an anticancer treatment sensitizer for a tumor, a blood thinner before an operation, a filling solution for an extracorporeal circulation circuit such as an artificial heart-lung machine, a perfusate for a replacement organ, an oxygen supplying solution to an ischemic site (myocardial infarction, cerebral infarction, respiratory insufficiency, etc.), a chronic anemia treating agent, and a perfusate for liquid ventilation. Also, when used as a gas absorbent, an oxidation reduction catalyst, an oxygen oxidation reaction catalyst, an oxygen addition reaction catalyst, since the oxygenated form is stable as compared to a conventional serum albumin-heme complex, the oxygen supply amount can be accurately controlled.

Moreover, the artificial oxygen carrier having the hemoglobin-albumin complex of the invention as an active component can also be applied to a patient with a rare blood type, an operation of an animal, and the like.

EXPLANATION OF REFERENCES

10 Hemoglobin
20 Albumin
100 Hemoglobin-Albumin Complex (Star-Shaped Heterocluster)

What is claimed is:

1. A hemoglobin-albumin complex having hemoglobin as the core, and albumin as the shell bound via a crosslinker to the hemoglobin,
wherein a binding site to the crosslinker in the albumin is cysteine 34.

2. The hemoglobin-albumin complex according to claim 1, wherein the binding site to the crosslinker in the hemoglobin is lysine.

3. The hemoglobin-albumin complex according to claim 1, wherein the bond between the hemoglobin and the crosslinker is an amide bond, and the bond between the albumin and the crosslinker is any of a disulfide bond or a sulfide bond.

4. The hemoglobin-albumin complex according to claim 1, wherein the number of the albumin is 1 to 7.

5. The hemoglobin-albumin complex according to claim 1, wherein the hemoglobin is at least one kind selected from the group consisting of human hemoglobin, bovine hemoglobin, recombinant human hemoglobin, and intramolecular crosslinked hemoglobin.

6. The hemoglobin-albumin complex according to claim 1, wherein the albumin is at least one kind selected from the group consisting of human serum albumin, bovine serum albumin, and recombinant human serum albumin.

7. The hemoglobin-albumin complex according to claim 1, wherein the crosslinker is at least one kind selected from the group consisting of compounds represented by the following general formulae (1) to (3) and chemical formula (1):

General Formula (1)

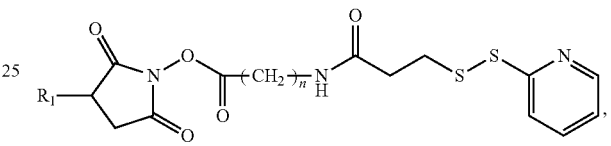

wherein in the general formula (1), R$_1$ represents any of a hydrogen atom or SO$_3^-$Na$^+$, and n represents an integer of 1 to 10;

Chemical Formula (1)

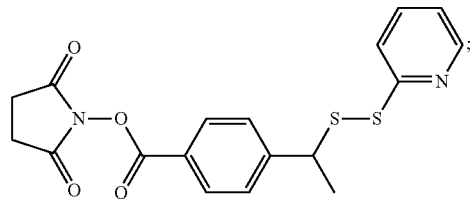

General Formula (2)

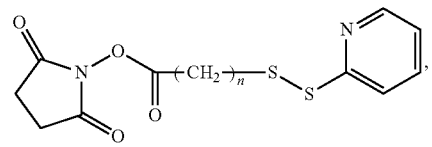

wherein in the general formula (2), n represents an integer of 1 to 10;

General Formula (3)

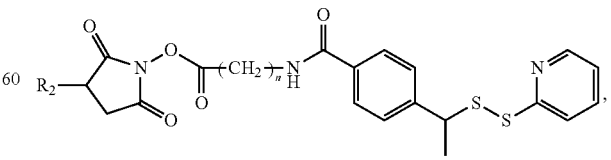

wherein in the general formula (3), R$_2$ represents any of a hydrogen atom or SO$_3^-$Na$^+$, and n represents an integer of 1 to 10.

8. The hemoglobin-albumin complex according to claim 1, wherein the crosslinker is represented by the following general formula (4):

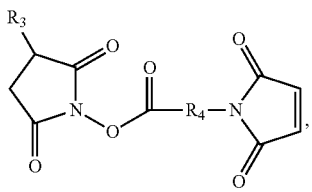

General Formula (4)

wherein in the general formula (4), $R_3$ represents any of a hydrogen atom or $SO_3^-Na^+$, and $R_4$ represents any of the following general formulae (5) to (6), or the following chemical formulae (2) to (4):

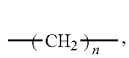

General Formula (5)

wherein in the general formula (5), n represents an integer of 1 to 10;

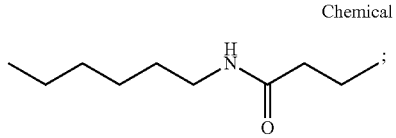

Chemical Formula (2)

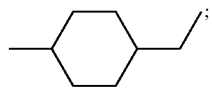

Chemical Formula (3)

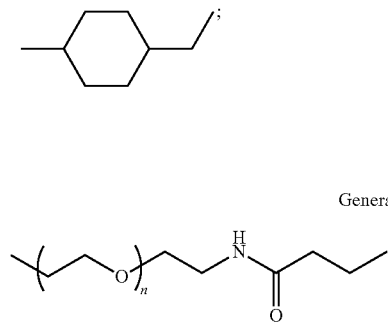

General Formula (6)

wherein in the general formula (6), n represents an integer of 2, 4, 6, 8, 10 or 12;

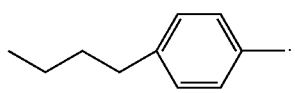

Chemical Formula (4)

9. An artificial plasma expander containing the hemoglobin-albumin complex according to claim 1.

10. An artificial oxygen carrier containing the hemoglobin-albumin complex according to claim 1.

* * * * *